(12) United States Patent
Keusenkothen et al.

(10) Patent No.: US 8,748,686 B2
(45) Date of Patent: Jun. 10, 2014

(54) CONVERSION OF CO-FED METHANE AND LOW HYDROGEN CONTENT HYDROCARBON FEEDSTOCKS TO ACETYLENE

(75) Inventors: Paul F. Keusenkothen, Houston, TX (US); Frank Hershkowitz, Liberty Corner, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 760 days.

(21) Appl. No.: 12/323,132

(22) Filed: Nov. 25, 2008

(65) Prior Publication Data
US 2010/0130803 A1 May 27, 2010

(51) Int. Cl.
 C07C 2/78 (2006.01)
 C07C 4/04 (2006.01)
 C07C 11/24 (2006.01)

(52) U.S. Cl.
 USPC ........... 585/540; 585/534; 585/535; 585/538; 585/539; 585/943

(58) Field of Classification Search
 USPC ............... 585/534, 535, 540, 538, 539, 943; 48/198.2
 See application file for complete search history.

(56) References Cited

U.S. PATENT DOCUMENTS

| 1,723,679 A | 8/1929 | Coberly et al. |
| 1,843,965 A | 2/1932 | Wulff |
| 1,880,306 A | 10/1932 | Wulff |
| 1,880,307 A | 10/1932 | Wulff |
| 1,880,308 A | 10/1932 | Wulff |
| 1,880,309 A | 10/1932 | Wulff |
| 1,880,310 A | 10/1932 | Wulff |
| 1,917,627 A | 7/1933 | Wulff |
| 1,938,991 A | 12/1933 | Wulff |

(Continued)

FOREIGN PATENT DOCUMENTS

| BE | 491 423 | 10/1949 |
| CA | 306 263 | 12/1930 |

(Continued)

OTHER PUBLICATIONS

Gannon, et al., "Acetylene" in Kirk-Othmer Encyclopedia of Chemical Technology, John Wiley, 2003, available on-line Apr. 18, 2003.*

(Continued)

*Primary Examiner* — In Suk Bullock
*Assistant Examiner* — Bradley Etherton

(57) ABSTRACT

A process and apparatus are provided to produce acetylene from a feed stream of low hydrogen content hydrocarbons such as coal by: (a) blending the hydrocarbons with methane to provide a blended mixture containing at least about 12.5 wt % atomic hydrogen; (b) partially combusting the blended mixture in a reactor in the presence of a source of oxygen to provide a partially combusted mixture at or above a temperature sufficient to produce methyl radicals; (c) maintaining the partially combusted mixture at or above the temperature for a residence time sufficient to produce a product stream containing enhanced yields of acetylene without significant formation of coke or coke precursors; (d) cooling the product stream to reduce the temperature of the product stream within a time sufficiently brief to substantially arrest any cracking reactions and provide a cooled product stream; and (e) recovering acetylene from the cooled product stream. The acetylene can be converted to ethylene by a conventional hydrogenation process.

18 Claims, 1 Drawing Sheet

(56) References Cited

U.S. PATENT DOCUMENTS

| | | |
|---|---|---|
| 1,966,185 A | 7/1934 | Preisman |
| 1,966,779 A | 7/1934 | Wulff |
| 2,037,056 A | 4/1936 | Wulff |
| 2,080,767 A * | 5/1937 | Dreyfus .......................... 585/534 |
| 2,236,534 A | 4/1941 | Hasche |
| 2,236,555 A | 4/1941 | Wulff |
| 2,319,679 A | 5/1943 | Hasche et al. |
| 2,343,866 A | 3/1944 | Hincke |
| 2,558,861 A | 7/1951 | Liggett |
| 2,645,673 A | 7/1953 | Hasche |
| 2,678,339 A | 5/1954 | Harris |
| 2,692,819 A | 10/1954 | Hasche et al. |
| 2,706,210 A | 4/1955 | Harris |
| 2,718,534 A | 9/1955 | Harris |
| 2,767,233 A * | 10/1956 | Mullen, II et al. ............ 585/541 |
| 2,796,951 A | 6/1957 | Bogart |
| 2,813,919 A | 11/1957 | Pearce |
| 2,830,677 A | 4/1958 | Coberly |
| 2,845,335 A | 7/1958 | Hasche |
| 2,851,340 A | 9/1958 | Coberly et al. |
| 2,885,455 A | 5/1959 | Hennig |
| 2,886,615 A | 5/1959 | Lindahl |
| 2,908,733 A * | 10/1959 | Sage ........................... 585/540 |
| 2,920,123 A | 1/1960 | Oldershaw et al. |
| 2,921,100 A | 1/1960 | Pettyjohn et al. |
| 2,956,864 A | 10/1960 | Coberly |
| 2,967,205 A | 1/1961 | Coberly |
| 3,024,094 A | 3/1962 | Coberly |
| 3,093,697 A | 6/1963 | Kasbohm et al. |
| 3,156,733 A | 11/1964 | Happel et al. |
| 3,156,734 A | 11/1964 | Happel |
| 4,200,682 A | 4/1980 | Sederquist |
| 4,256,565 A * | 3/1981 | Friedman et al. ............. 208/129 |
| 4,264,435 A | 4/1981 | Read, Jr. et al. |
| 4,536,603 A * | 8/1985 | Sprouse et al. ............... 585/539 |
| 4,640,675 A * | 2/1987 | Green et al. ...................... 431/2 |
| 4,714,796 A | 12/1987 | Senkan |
| 4,724,272 A | 2/1988 | Raniere et al. |
| 4,754,095 A | 6/1988 | Coughenour et al. |
| 4,973,777 A | 11/1990 | Alagy et al. |
| 5,068,486 A | 11/1991 | Han et al. |
| 5,138,113 A | 8/1992 | Juguin et al. |
| 5,824,834 A * | 10/1998 | Bachtler et al. ............... 585/540 |
| 5,886,056 A | 3/1999 | Hershkowitz et al. |
| 5,935,489 A | 8/1999 | Hershkowitz et al. |
| 5,976,352 A | 11/1999 | Busson et al. |
| 6,027,635 A | 2/2000 | Busson et al. |
| 6,076,487 A | 6/2000 | Wulff et al. |
| 6,287,351 B1 | 9/2001 | Wulff et al. |
| 6,365,792 B1 * | 4/2002 | Stapf et al. .................... 585/539 |
| 6,575,147 B2 | 6/2003 | Wulff et al. |
| 6,632,351 B1 | 10/2003 | Ngan et al. |
| 2002/0020113 A1 | 2/2002 | Kennedy et al. |

FOREIGN PATENT DOCUMENTS

| | | | |
|---|---|---|---|
| EP | 1741691 A1 * | 1/2007 | ............... C07C 2/82 |
| FR | 841 410 | 2/1939 | |
| FR | 1 588 738 | 4/1970 | |
| GB | 763675 | 12/1956 | |
| GB | 830 574 | 3/1960 | |
| GB | 855 764 | 12/1960 | |
| GB | 972153 | 10/1964 | |
| GB | 1064447 | 4/1967 | |
| GB | 1149798 | 4/1969 | |
| GB | 959818 | 6/1994 | |
| WO | WO 01/70913 | 9/2001 | |

OTHER PUBLICATIONS

Paessler, et al., "Acetylene" in Ullmann's Encyclopedia of Industrial Chemistry, 2002, Wiley-VCH, available on-line on Oct. 15, 2008.*

Crelling, et al., "Coal" in Ullmann's Encyclopedia of Industrial Chemistry, 2002, Wiley-VCH, available on-line on Apr. 15, 2010.*

Bartholome, V.E., "*Methods of Energy Addition for Endothermic Gas Reactions at High Temperatures*", Zeitschrift fuer Elektrochemie und Angewandte Physikalische Chemie, 57, pp. 497-502 (1953).

Bixler, G.H. et al. "*Wulff Process Acetylene*", Journal of Industrial and Engineering Chemistry, Washington, D.C., 45, pp. 2596-2606 (1953).

Bogart, M.J.P. et al., "*Recent Developments in Wulff Acetylene*", Chemical Engineering Progress, 50, pp. 372-375 (1954).

Bogart, M.J.P. et al., "*The Wulff Process for Acetylene from Hydrocarbons*", Petroleum Processing, 8, pp. 377-382 (1953).

Garifzyanova, G.G. et al., "*Pyrolysis of Vacuum Resid by the Plasma Chemical Method*," Chemistry and Technology of Fuels and Oils, vol. 42, No. 3, pp. 172-175 (2006).

Holmen, A. et al., "*Pyrolysis of natural gas: chemistry and process concepts*", Fuel Processing Technology, 42, Elsevier Science B.V., pp. 249-267 (1995).

Jennings, R.J.S., "*Organic Chemicals from Natural Gas-I*", Chemical & Process Engineering, 33, pp. 243-246 (1952).

Kinney, C.R. et al. "*On the Mechanism of Carbonization of Benzene, Acetylene and Diacetylene at 1200° C.*", Proc. 4$^{th}$ Carbon Conference, Pergamon Press, pp. 301-313 (1960).

Sherwood, V.P.W. et al., "*Acetylene from Natural Gas and Petroleum*", Erdoel und Kohle 7, pp. 819-822 (1954).

Sneddon, R., "*Successful Acetylene Synthesis*", The Petroleum Engineer, 26, pp. C5-C8 (1954).

Weaver, T. "*Economics of Acetylene by Wulff Process*", Processing Engineering, Chemical Chemical Engineering Progress. 49, pp. 35-39 (1953).

* cited by examiner

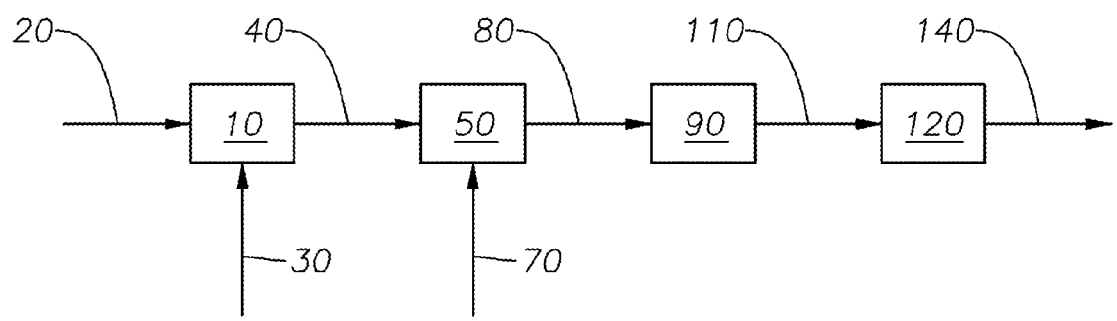

CONVERSION OF CO-FED METHANE AND LOW HYDROGEN CONTENT HYDROCARBON FEEDSTOCKS TO ACETYLENE

FIELD OF THE INVENTION

This invention pertains to conversion of low hydrogen content hydrocarbons such as coal by blending with methane and treating the resulting blend in a partial oxidation reactor utilizing oxygen as a cofeed, to produce acetylene.

BACKGROUND

Conventional steam crackers are known as an effective tool for cracking high-quality feedstocks that contain a large fraction of volatile hydrocarbons, such as ethane, gas oil, and naphtha. Regenerative pyrolysis reactors are also known and conventionally used for converting or cracking and to execute cyclic, high temperature chemistry such as those reactions that may be performed at temperatures higher than can suitably be performed in conventional steam crackers. Regenerative reactor cycles typically are either symmetric (same chemistry or reaction in both directions) or asymmetric (chemistry or reaction changes with step in cycle). Symmetric cycles are typically used for relatively mild exothermic chemistry, examples being regenerative thermal oxidation ("RTO") and autothermal reforming ("ATR"). Asymmetric cycles are typically used to execute endothermic chemistry, and the desired endothermic chemistry is paired with a different chemistry that is exothermic (typically combustion) to provide heat of reaction for the endothermic reaction. Examples of asymmetric cycles are Wulff cracking, Pressure Swing Reforming, and other regenerative pyrolysis reactor processes. Regenerative pyrolysis reactors are generally known in the art as being capable of converting or cracking hydrocarbons. However, they have not achieved commercial or widespread use for hydrocarbon conversion, due at least in part to the fact that they have not scaled well to an economical size. This failure is in large part due to the inability of the equipment to adequately control and contend with the very high temperatures and the way that fuel and oxidant are combined during the regeneration or heating stage of the process. The high temperatures are difficult to position and contain for extended periods of time and lead to premature equipment failure. A solution was proposed in a patent application filed in the U.S.P.T.O., on Dec. 21, 2006, entitled "Methane Conversion to Higher Hydrocarbons," (2006EM215US), Ser. No. 11/643,541 related primarily to methane feedstocks for pyrolysis systems, utilizing an inventive deferred combustion process with a reverse-flow reactor system. U.S. Patent Application Ser. No. 60/933,044, filed Jun. 4, 2007 (2007EM150PRV), entitled "Pyrolysis Reactor Conversion of Hydrocarbon Feedstocks into Higher Value Hydrocarbons," teaches removing nonvolatiles from a pyrolysis feed prior to its introduction to the pyrolysis reactor, wherein fuel and oxygen are added in a first reactor to provide heat to a second reactor in which a hydrocarbon feed is pyrolyzed. U.S. Application Ser. No. 60/933,011, filed Jun. 4, 2007 (2007EM151PRV), entitled "Conversion of Co-Fed Methane and Hydrocarbon Feedstocks into Higher Value Hydrocarbons," teaches removing nonvolatiles from a pyrolysis feed to provide a vapor phase which is fed with methane to a pyrolysis reactor system to provide acetylene. All of the foregoing U.S. patent applications are incorporated herein by reference in their entirety.

As with steam crackers, regenerative pyrolysis reactors are well suited for volatized or volatizable feedstocks that are substantially free of nonvolatile components, such as metals and other residual or nonvolatizable components, which would otherwise lay down and build up in the reactor as ash. Pyrolysis reactors typically operate at higher temperatures than steam crackers.

Typically, regenerative reactors include a reactor bed or zone, typically comprising some type of refractory material, where the reaction takes place within the reactor system. Conventional regenerative reactors typically deliver a stream of fuel, oxidant, or a supplemental amount of one of these reactants, directly to a location somewhere within the flow path of the reactor bed. The delivered reactants then are caused to exothermically react therein and heat the reactor media or bed. Thereafter, the reacted reactants are exhausted and a pyrolysis feedstock, such as a hydrocarbon feed stream, preferably vaporized, is introduced into the heated region of the reactor media or bed, and exposed to the heated media to cause heating and pyrolysis of the reactor feedstock into a pyrolyzed reactor feed. The pyrolyzed reactor feed is then removed from the reaction area of the reactor and quenched or cooled, such as in a quench region of the reactor system, to halt the pyrolysis reaction and yield a pyrolysis product. Such an arrangement requires a dedicated fuel to heat the reactor bed, which fuel is separate from the feed which is to be pyrolyzed and so introduces additional complexity to the operation.

"On the Mechanism of Carbonisation of Benzene, Acetylene and Diacetylene at 1200° C.", Kinney, C. R. & Slysh, R. S. 1960 Proc. 4th Carbon Conference, Pergamon Press, at p. 301 et seq., teaches conversion of methane at reasonable yields to acetylene and ethylene through methyl radical and hydrogen radical intermediates at 2000° C. Heavier hydrocarbons can be converted to acetylene and syngas at temperatures above 2000° C., but if their hydrogen content is low, the reaction yields significant coke. Benzene with hydrogen content of less than 8% yields only 18 wt % $C_2$, and 70 wt % carbon at 70% conversion, 1200° C., and 56 milliseconds. The reaction is preferentially carried out in the presence of hydrogen (hydropyrolysis) to further reduce soot formation for aromatic feeds.

Garifzyanova and Garifzyanov report in the "Pyrolysis of Resid by the Plasma Chemical Method," Chem. Tech. Fuels & Oils 42, p. 172 (2006) that pyrolyzing vacuum resid feed containing 10% atomic hydrogen content with a hydrogen methane plasma acting as a hydrogen donor improves $C_2$ yields in the product. The plasma generates hydrogen radicals.

Heavy hydrocarbon liquids can be used in feedstocks for thermal cracking, as well as solid hydrocarbonaceous materials. U.S. Pat. No. 4,536,603 to Sprouse et al., whose contents are incorporated herein by reference in their entirety, discloses a process for reacting coal with a hot gas stream to produce acetylene by reacting fuel, oxygen and steam to provide a hot gas stream that is accelerated and impinged upon a stream of particulate bituminous or subbituminous coal, and the resulting mixture decelerated to produce a product stream. The acceleration and deceleration can be carried out in a convergent-divergent nozzle. U.S. Pat. No. 4,256,565 to Friedman et al., whose contents are incorporated herein by reference in their entirety, teaches the production of olefins from low hydrogen content heavy hydrocarbons containing aromatics such as petroleum residua, asphalts and heavy gas oils. Hydrogen and oxygen are reacted in a first reaction zone to provide a heated gas stream of hydrogen and water at 1000° to 2000° C. which is reacted with sprayed hydrocarbon feed to provide within 2 milliseconds a reaction mixture of 800° to 1800° C. which is maintained for 1 to 10 milliseconds to form enhanced yields of olefins and then quenched. U.S. Pat. No. 6,365,792 to Stapf et al., whose contents are incorporated herein by reference in their entirety, discloses the preparation of acetylene and synthesis gas by thermal treatment of a starting mixture, e.g., methane, higher hydrocarbons and molecular oxygen which mixture is heated to a maximum of 1400° C., brought to reaction in a reactor and cooled, with less solid carbon being formed. U.S. Pat. No. 4,264,435 to Read et al., whose contents are incorporated herein by reference in their entirety, teaches cracking crude oil in an adiabatic reactor utilizing a partial combustion zone generating hydrogen, carbon monoxide, carbon dioxide, and water. Injection of superheated or shift steam into the burner or combustion gases produces more carbon dioxide and hydrogen by the shift reaction, and subsequent injection of crude oil enhances olefins and aromatics production while minimizing coking. Heavy oils generated by the process can be used as fuel for the partial combustion burner. Such low hydrogen content hydrocarbon materials when converted at reasonable yields to acetylene and ethylene at temperatures below 1400° C. result in significant coke formation.

U.S. Pat. No. 5,068,486 to Han et al. reveals a partial oxidation process that operates at very high pressure (20-100 atm), necessitating very high compression costs. The conversion of methane, which is the hydrocarbon feed, is reported as 12.6%, with hydrocarbon selectivity of 32%. The overall conversion of methane to ethylene, acetylene, and propane were 1.4%, 0.4% and 0.1%, respectively. U.S. Pat. Nos. 5,886,056 and 5,935,489 to Hershkowitz et al. teach a multi-nozzle design for feeding a partial oxidation reactor. The multiple nozzles allow introduction of a pre-mix of oxidant and fuel at the burner face so that these gases are premixed and of uniform composition.

It would be highly desirable to provide a process which is suited not only to pyrolysis of heavy liquid feeds containing non-volatiles, but also to other low hydrogen content hydrocarbons including hydrocarbonaceous solids, e.g., coal. Moreover, it would be desirable to carry out such a process utilizing the hydrocarbonaceous feed itself or a component thereof as a source of heat to effect the pyrolysis, in such a way as to minimize coke and tar formation.

SUMMARY

The present invention provides a process for preparing acetylene from low hydrogen content hydrocarbons, including coal, by mixing with methane to form a blended mixture of increased hydrogen content and partially combusting the blend in a reactor in the presence of a source of oxygen to form a heated partially combusted mixture at or above a temperature sufficient to produce methyl radicals and maintaining the mixture for time sufficient to produce acetylene without substantial coke and tar formation.

In one aspect, the present invention relates to a process for producing acetylene by pyrolysis from a feed stream of hydrocarbons containing less than about 12 wt % atomic hydrogen, the process comprising: (a) blending the hydrocarbons containing less than about 12 wt % atomic hydrogen with methane to provide a blended mixture containing at least about 12.5 wt % atomic hydrogen; (b) partially combusting the blended mixture in a reactor in the presence of a source of oxygen, the oxygen being provided in an amount less than the stoichiometric amount required to combust with all of the blended mixture to provide a partially combusted mixture at or above a temperature sufficient to produce methyl radicals; (c) maintaining the partially combusted mixture in the substantial absence of oxygen at or above the temperature for a residence time sufficient to convert the mixture to a product stream containing enhanced yields of acetylene without significant formation of coke and/or coke precursors; (d) cooling the product stream to reduce the temperature of the product stream within no greater than 100 milliseconds to substantially arrest any pyrolysis reactions and provide a cooled product stream; and (e) recovering acetylene from the cooled product stream.

In an embodiment of this aspect of the invention, at least a portion of acetylene derived from the cooled product stream is converted to ethylene by hydrogenation.

In certain embodiments of this aspect of the invention, the cooling is carried out by passing the product stream through at least one of a) a convergent-divergent nozzle, b) a gas turbine expander, c) an indirect heat exchanger, d) a direct liquid quench zone, and e) an endothermic reactant addition zone. In one embodiment, the cooling is carried out by passing the product stream through a convergent-divergent nozzle in which the product stream is accelerated to a velocity of at least about 150 meters per second and decelerated to a velocity no greater than about 100 meters per second in the converging-diverging nozzle. In a particular embodiment, the product stream is accelerated to a velocity ranging from about 150 to about 1220 meters per second and decelerated to a velocity ranging from about 45 to about 100 meters per second, the product stream being cooled in less than about 2 milliseconds, to provide a cooled product stream of no greater than about 260° C. In yet another embodiment of this aspect of the invention, a quench liquid is introduced between the convergent and divergent sections of the nozzle. The quench liquid in the direct liquid quench zone can be selected from water and hydrocarbon. In an embodiment wherein the cooling is carried out by passing the product stream through an endothermic reactant addition zone, ethane can be added to the endothermic reactant addition zone.

In another embodiment of this aspect of the invention, the partially combusted mixture is maintained at or above 1600° C. for a residence time of no greater than about 100 milliseconds, and, optionally, the product stream is cooled in less than about 10 milliseconds, to provide a cooled product stream of no greater than about 482° C. Typically, the partially combusted mixture is maintained at or above 2000° C. for a residence time of no greater than about 50 milliseconds, the product stream is accelerated to a velocity ranging from about 150 to about 1220 meters per second and decelerated to a velocity ranging from about 45 to about 100 meters per second and the product stream is cooled in less than about 2 milliseconds, to provide a cooled product stream of no greater than about 260° C. The partially combusted mixture can be maintained at or above 2000° C. for a residence time ranging from about 2 to about 30 milliseconds.

In another embodiment of this aspect of the invention, step (c) is carried out in the presence of sufficient hydrogen to reduce formation of coke or coke precursors beyond that produced in the absence of hydrogen.

In still another embodiment of this aspect of the invention, the feed stream of hydrocarbons is selected from the group consisting of aromatic feed, gas oils, cracked gas oils, crude, atmospheric resid feed, vacuum resid feed, tars, heavy feed containing pitch, and coal. The feed stream of hydrocarbons can comprise coal particles having a median particle size of less than about 100 microns in diameter, say, e.g., less than about 75 microns in diameter, say, from about 10 to about 60 microns in diameter. Typically, the feed stream of hydrocarbons contains less than about 11 wt % atomic hydrogen, e.g., less than about 8 wt % atomic hydrogen.

In yet still another embodiment of this aspect of the invention, syngas is also recovered from the cooled product stream.

In still yet another embodiment of this aspect of the invention, ethylene is recovered from the cooled product stream.

In another embodiment of the invention, at least a portion of the product stream containing acetylene can be converted to ethylene by hydrogenation, typically using vapor phase or liquid phase hydrogenation technology.

In another embodiment of this aspect of the invention, the partially combusted mixture is provided at or above a temperature sufficient to produce methyl radicals and hydrogen radicals.

In another aspect, the present invention relates to an apparatus for producing acetylene by pyrolysis from a feed stream of hydrocarbons containing less than about 12 wt % atomic hydrogen, the apparatus comprising: (a) a mixing zone for blending the hydrocarbons containing less than about 12 wt % atomic hydrogen with methane to provide a blended mixture containing at least about 12.5 wt % atomic hydrogen; (b) a partial combustion zone for partially combusting the blended mixture comprising a source of oxygen, the oxygen being provided in an amount no greater than 50 wt % of the stoichiometric amount required to fully combust all of the blended mixture and capable of providing a partially combusted mixture at or above a temperature sufficient to provide methyl radicals; (c) a pyrolysis zone for maintaining the partially combusted mixture in the substantial absence of oxygen at or above the temperature for a residence time sufficient to produce a product stream containing enhanced yields of acetylene without significant formation of coke or coke precursors; (d) a cooling zone for cooling the product stream in no greater than 100 milliseconds to substantially arrest any cracking reactions and provide a cooled product stream; and (e) a recovery zone for recovering acetylene from the cooled product stream.

In one embodiment of this aspect of the invention, the apparatus further comprises: f) a hydrogenation zone for hydrogenating at least a portion of acetylene from the cooling zone or recovery zone for conversion to ethylene.

In another embodiment of this aspect of the invention, the cooling zone comprises at least one of 1) a convergent-divergent nozzle, 2) a gas turbine expander, 3) an indirect heat exchanger, 4) a direct liquid quench zone, and 5) an endothermic reactant addition zone.

BRIEF DESCRIPTION OF THE DRAWING

FIG. 1 is a simplified schematic illustration of the partial combustion process and reactor system according to the present invention.

DETAILED DESCRIPTION

The term "convert" is defined broadly herein to include any molecular decomposition, cracking, breaking apart, conversion, and/or reformation of organic molecules in the hydrocarbon feed, by means of at least pyrolysis heat, and may optionally include supplementation by one or more of catalysis, hydrogenation, diluents, and/or stripping agents.

For present purposes, the term "pyrolysis" relates to the chemical decomposition of organic materials by heating in the absence of oxygen or any other reagents, except possibly steam. Pyrolysis can occur in the absence of water (anhydrous pyrolysis) or in the presence of water (hydrous pyrolysis). Pyrolysis typically occurs under pressure and at operating temperatures above 430° C. (800° F.). In practice, it is not possible to achieve a completely oxygen-free atmosphere. Because some oxygen is present in any pyrolysis system, a small amount of oxidation typically occurs.

The low hydrogen content feed stream of hydrocarbons treated in accordance with the present invention contains less than about 12 wt % atomic hydrogen, based on the weight of hydrogen atoms in the hydrocarbons, compared to the overall weight of the hydrocarbons. The hydrogen content of feeds, reactants and products for present purposes can be measured using any suitable protocol, e.g., ASTM D1018-00 (2005) Standard Test Method for Hydrogen in Petroleum Fractions. Testing the hydrogen content of hydrocarbonaceous solids, e.g., coal, can be carried out using ASTM D5373-08 Standard Test Methods for Instrumental Determination of Carbon, Hydrogen, and Nitrogen in Laboratory Samples of Coal.

Examples of the low hydrogen content hydrocarbon feedstocks include one or more of steam cracked gas oil and residues, gas oils, heating oil, jet fuel, diesel, kerosene, gasoline, coker naphtha, steam cracked naphtha, catalytically cracked naphtha, hydrockrackate, reformate, raffinate reformate, distillate, crude oil, atmospheric pipestill bottoms, vacuum pipestill streams including bottoms, wide boiling range naphthas, heavy non-virgin hydrocarbon streams from refineries, vacuum gas oil, heavy gas oil, naphtha contaminated with crude, atmospheric resid, heavy residuum, $C_4$'s/ residue admixture, condensate, contaminated condensate, naphtha residue admixture and mixtures thereof. The low hydrogen content hydrocarbon feedstock may have a nominal end boiling point of at least 400° F. (204° C.), (e.g., greater than or equal to 400° F., such as in excess of 1200° F. and even in excess of 1500° F.) and will commonly have a nominal end boiling point of at least 500° F. (260° C.). Some preferred hydrocarbon feedstocks include crude oil, atmospheric resids, contaminated condensate, and gas oil distillates, tars, fuel oils and cycle oils. Such heavier, more aromatic feeds are typically lower cost, per unit weight, but may yield lower acetylene and ethylene yields and higher carbon or tar yields. Especially preferred feeds include aromatic feed, gas oils, cracked gas oils, crude, atmospheric resid feed, vacuum resid feed, tars, and heavy feed containing pitch. Due to the high aromatic content of the heavier feeds, the feeds have low hydrogen content (typically less than about 8 wt % atomic hydrogen content). During pyrolysis, the hydrogen deficient feeds may form tar, coke, or soot.

The invention is also suitable for other carbonaceous fluid or finely divided solid fuels which can be partially combusted, such as lignite, pulverized wood, bitumen, soot, petroleum coke, and coal. For present purposes, the coal can be a particulate coal having a median particle size less than about 100 microns and preferably less than about 75 microns. While the coal can come from any suitable source, it is preferred that the coal be selected from the group consisting of bituminous and subbituminous coals which are believed to provide higher yields of acetylene. The coal can be ground such that 80 wt % will pass through a 200 mesh screen, providing a coal with median particle size of less than about 75 microns.

Methane, including a methane-containing feed, may be blended (e.g., mixed, commingled, introduced, fed into, or otherwise combined) into the low hydrogen content feed stream at a point upstream of or within the location at which partial combusting occurs. A convenient place for introduction of the methane-containing feed may be a transfer line. If the methane source is a hydrocarbon stream that comprises methane, the stream should comprise at least 10 weight percent methane, preferably at least 30 weight percent methane, and more preferably at least fifty weight percent methane.

Other alkanes, such as ethane, may also be present. Methane is blended with the low hydrogen content feed stream of hydrocarbons in an amount sufficient to provide a blend with an overall atomic hydrogen content of at least about 12.5 wt %, preferably at least about 14 wt %, e.g., at least about 15 wt %. Preferred methane to low hydrogen content hydrocarbon feed weight ratios may range from about 0.1 to about 2, say, from about 0.2 to about 1.0.

The blended mixture containing methane and low hydrogen content hydrocarbon feed stream can include substantially any other hydrocarbon co-feed material that undergoes endothermic reforming, such as reforming to acetylene, including natural gas mixtures, other petroleum alkanes, petroleum distillates, kerosene, jet fuel, fuel oil, heating oil, diesel fuel and gas oil, gasoline, and alcohols. A preferred co-feed may be a hydrocarbon component that may function as a hydrogen donor diluent, such as tetralin, and dihydroanthracene, hydropyrene, or hydrotreated steam cracked tar oils. Preferably, the feed will be in a vapor or gaseous state at the temperature and pressure of introduction into the reactor system.

The amount of nonvolatiles present in the low hydrogen content hydrocarbon feedstream will vary depending upon the feedstock source and quality. Crude oil and atmospheric residue often contain high molecular weight, nonvolatiles with boiling points in excess of about 1100° F. (593° C.), otherwise known as resids. For example, contaminates, full range vacuum gas oils, and petroleum crude oils often contain relatively high levels of nonvolatile molecules, for example, up to 20 percent by weight of nonvolatiles. Other feedstocks may contain even higher concentrations of nonvolatiles. A typical hydrocarbon feedstock used in the process of the present invention may contain nonvolatiles in an amount of from about 5 to about 40 weight percent based upon the weight of the total hydrocarbon feed. If using a coal-containing feedstock, the amount of nonvolatiles present can be even greater than about 40 weight percent, e.g., greater than about 50 weight percent, or even greater than about 60 weight percent, based upon the weight of the total hydrocarbon feed. Feeding a hydrogen diluent should help offset the presence of nonvolatiles to facilitate production of preferred products, such as acetylene and ethylene.

In the partial combustion step, the source of oxygen may be pure oxygen or a gas containing molecular oxygen. Molecular oxygen is usually provided to the starting mixture as a component of air or air/oxygen mixtures. In order to effect the desired partial combustion of the present invention, it is desired that the oxygen be introduced in an amount less than the stoichiometric amount, i.e., that amount required to react with all the hydrocarbonaceous components in the blended mixture of low hydrogen content hydrocarbons and methane. Generally, the total oxygen introduced is no greater than about 50 wt % and typically ranges from about 10 wt % to about 50 wt %, preferably from about 20 wt % to about 40 wt % of the stoichiometric amount, i.e., the amount of molecular oxygen needed to effect complete combustion of all the blended mixture. The partially combusted mixture is then converted to a product stream of enhanced acetylene content in the substantial absence of oxygen, i.e., the oxygen is present in amounts below that needed to sustain additional combustion. Typically, such amounts are no greater than 100 wppm, e.g., no greater than about 10 wppm oxygen. "Partial combustion" for present purposes is carried out by reacting a fluid or solid carbonaceous reactant fuel with oxygen to provide heat and normally gaseous products of combustion. The reactant, acting as a fuel, contains mainly carbon and hydrogen, which react with the supplied oxygen and, in some cases, with steam and carbon dioxide, to form carbon monoxide and hydrogen. The hot gas stream produced by partial combustion is essentially free of oxygen, i.e., in amounts less than about 0.2 volume percent of the total gas stream produced.

Partial combustion provides an elevated temperature for the partially combusted mixture sufficient to provide methyl radicals in the mixture. The methyl radicals are believed useful in the formation of the desired acetylene product. Such temperatures typically can range from about 1600° to about 2000° C., preferably from about 1700° to about 1900° C. Pressures during partial combustion can range from about subambient to about 1000 kPa, preferably from about 1 to about 500 kPa. The partially combusted mixture is maintained at or above the aforementioned temperatures for a residence time of no greater than about 100 milliseconds, preferably no greater than about 50 milliseconds, e.g., no greater than about 10 milliseconds, say, no greater than about 5 milliseconds. The partially combusted mixture is typically maintained under these conditions to produce a product stream containing enhanced yields of acetylene without significant formation of coke and/or coke precursors. Typical yields of acetylene in the product stream can range from at least about 5 wt % acetylene, preferably from at least about 8 wt % acetylene, e.g, at least about 15 wt % acetylene, say, from about 5 wt % acetylene to about 20 wt % acetylene, based on the total weight of the effluent leaving the reactor. Coke precursors are large condensable molecules that condense in the vapor, and then form coke under typical operating conditions encountered in the present process of the invention. Included among coke precursors are asphaltenes, which are n-heptane insoluble components. Asphaltene content of a sample can be determined by well-known analytic techniques, e.g., ASTM D6560 (Standard Test for Determination of Asphaltenes (Heptane Insolubles) in Crude Petroleum and Petroleum Products), or ASTM D3270 (Standard Test Method for n-Heptane Insolubles). For present purposes, "significant" formation of coke and/or coke precursors is formation to an extent that is deleterious to the operation of the present invention, e.g., resulting in a need to interrupt operation of the invention to remove accumulated coke deposits. Typically, a product stream, other than that obtained from coal-containing feed "without significant formation of coke and/or coke precursors" contains no greater than about 1000 ppm, preferably no greater than about 100 ppm by weight, of coke and/or coke precursors.

Partial combustion can also be carried out to produce a temperature sufficient to provide hydrogen radicals in the partially combusted mixture, which can react with low hydrogen content hydrocarbon feed stream to provide hydrocarbon molecules of enhanced hydrogen content. Such a temperature typically ranges from about 1300° to about 2400° C., preferably from about 1400° to about 2000° C.

In certain embodiments, the gaseous product stream may be contacted with a reactant, such as a hydrogen-containing material, that may be injected into the pyrolysis or cracking zone. The particular material used as the reactant is not limited and may include, for example, air, water vapor, hydrogen gas, ammonia, and/or hydrocarbons.

The pyrolysis reaction for the preparation of acetylene gas can be carried out by the process according to the invention at any desired pressure, preferably at atmospheric pressure. Suitable reactors are preferably flame reactors, regenerative reactors (e.g., reverse-flow reactors including those applied to partial oxidation in the symmetric cycle as earlier noted), recuperative reactors (e.g., a reactor system using effluent heat to warm feeds) and flow reactors, in particular tubular reactors. Flame reactors employed frequently have a swirl burner or a burner block with subsequent combustion chamber. Suitable flame reactors operate, for example, with a pre-mixing flame or diffusion flame. Flow reactors employed frequently contain a pre-mixing flame. The residence time in the reactor is generally shorter than 100 milliseconds.

The product stream containing enhanced yields of acetylene is cooled to reduce its temperature from that maintained at the outlet of the pyrolysis reactor, within a time sufficiently brief to substantially arrest any cracking reactions, e.g., the formation of soot. Typically, such cooling, which can include quenching, can be carried out in less than about 100 milliseconds, typically less than about 10 milliseconds, say, less than about 2 milliseconds. This rapid cooling can be effected by passing the product to be cooled through at least one of a) a convergent-divergent nozzle, b) a gas turbine expander, c) an indirect heat exchanger, d) a direct liquid quench zone and e) an endothermic reactant addition zone.

The hot product stream can be cooled using Joule-Thompson adiabatic and isentropic expansion through, for example, the use of a convergent-divergent nozzle or a "virtual" convergent-divergent nozzle. Use of a convergent-divergent nozzle for quenching reduces temperature by converting thermal energy of the treated stream into kinetic energy of unidirectional velocity, without actually removing total energy from the stream. Systems suited to use in the present invention using convergent-divergent nozzles are disclosed in U.S. Pat. No. 4,256,565 to Friedman et al., U.S. Pat. No. 4,264,435 to Read et al., and U.S. Pat. No. 4,536,603 to Sprouse et al., all of which are incorporated herein by reference in their entirety.

The hot product stream can also be cooled by passing it through a gas turbine expander in accordance with techniques familiar to those skilled in the art. Like convergent-divergent nozzles, gas turbine expanders convert temperature to velocity; however, they actually remove heat as work from the process. Suitable gas expander applications for use in the present invention are shown in U.S. Pat. No. 2,870,231 to Hughes et al., U.S. Pat. No. 2,632,689 to Latchum, U.S. Pat. No. 2,805,268 to Cunningham, U.S. Pat. No. 3,320,154 to Tokuhisa et al. and U.S. Pat. No. 3,329,605 to Tokuhisa et al., incorporated herein by reference in their entirety.

In an embodiment of the invention, the reaction gas product stream can be quenched or cooled rapidly on leaving the pyrolysis or cracking zone by direct quenching, in which a liquid (quench oil or water) or gaseous (e.g., steam or cold recycled gases) quenching agent is sprayed in directly. During this operation, the corresponding mixture is cooled to different extents depending on the quenching agent employed—typically to about 300° C. in the case of oil or hydrocarbon liquid as quenching agent, and to about 100° C. in the case of water as quenching agent.

It is possible to employ direct cooling of pyrolysis product, i.e. direct quenching, in the process of the invention. This can be carried out, for example, by spraying in quenching oil or water. However, indirect cooling using a heat exchanger is generally much more economical. The heated coolant can then be used, for example, to operate a high-pressure steam generator or a feedstock pre-heater. In principle, any type of heat exchanger which quenches sufficiently fast enough to preserve desired product, e.g., acetylene, made by partial oxidation can be used for the purpose of indirect cooling. High effectiveness heat exchangers for use in the present invention include transfer line exchangers, such as linear transfer line exchangers, characterized by a one to one connection between exchanger tube and radiant coil outlet in a furnace, e.g., Schmidt'sche Linear Exchangers, available from Alstom Power Energy Recovery, GmbH of Kassel, Germany.

Cooling can also be carried out by adding to the hot product stream an endothermic reactant such as an alkane, e.g., ethane, which undergoes endothermic reactions, e.g., olefin formation. Such a techniques is especially useful for high temperature quench where sufficient kinetics are available to alkanes for the endothermic reaction. Co-reaction of acetylene to ethylene, while economically attractive, tends to reduce the endothermicity and thus reduces quench effectiveness. U.S. Pat. No. 5,565,009 to Ruhl et al., U.S. Pat. No. 5,215650 to Sapre and EP 1741691 (SABIC) disclose endothermic reactant addition techniques for cooling hot hydrocarbon-containing streams and are incorporated herein by reference in their entirety.

Of these cooling techniques, the use of convergent-divergent nozzles and gas turbine expanders results in a reduction of stream pressure, while the remaining techniques maintain stream pressure. Accordingly, if higher target outlet pressures are desired, use of direct and indirect liquid quench, and endothermic reactant addition cooling techniques will be preferred. However, if optimization of acetylene is desired, the stream pressure reducing techniques are suitable because acetylene-producing chemistry tends to be more effective at lower pressures.

The cooled product is subsequently separated into desired end-products. Acetylene can be washed out of the resultant mixture by selective solvents, e.g., NMP (N-methyl pyrollidone), DMF (dimethyfornamide), kerosene, THF (tetrahydrofuran), acetone and other polar aprotic solvents, e.g., DMSO (dimethylsulfoxide). Separation of desired end-products can start at cooling where heavy components can be removed. Further, during cooling the gas obtained can be compressed, and acids and water can be removed using basic or MEA scrubbers and driers downstream of the compressors. Subsequently, the product can be dried and uncracked feed, ethane and propane may be recovered for recycling as pyrolysis feed. The cracking severity affects the composition of the product obtained.

Hydrocarbon products of the pyrolysis include, but are not limited to, acetylene, ethylene, propylyne, diacetylene, butadiene, benzene, and methane, and other associated acetylenic, olefinic, paraffinic, and aromatic products. Acetylene content of the hydrocarbon products typically ranges from about 5 to about 70 wt %, say, from about 10 to about 50 wt %, e.g., from about 20 to about 50 wt %.

Referring to the Figure, aromatic gas oil having a hydrogen content of less than about 9 wt % are introduced to blending zone 10 at ambient temperature at a rate of about 60 g per second through blending zone inlet 20. Methane gas is introduced at a temperature of about 200° C. to the blending zone through blending zone inlet 30 at a rate of 40 g per second which is sufficient to provide a blended coal/methane mixture of about 14 wt % hydrogen. Extensive mixing is effected by a sparger or atomizer. The blended mixture can be heated prior to partial combustion by any suitable means. For example, the heating can be conducted by means of a heat exchanger, steam injection, submerged heat coil, or a fired heater. The blended oil/methane mixture passes from the blending zone via line 40 into partial combustion zone 50, at a rate of about 100 g per second. Oxygen is introduced into partial combustion zone 50 in amounts of less than about 50% of the stoichiometric amount via oxygen inlet 70 at a rate of about 90 g per second, where oxygen temperature is measured. Partial combustion is initiated by ignition, e.g., spark. The partially combusted mixture which is substantially free of oxygen passes from an outlet of partial combustion zone 50 via line 80 at a temperature of at least about 1600° C. The partially combusted mixture is introduced to pyrolysis zone 90 through line 80 where the mixture is maintained at a temperature of at least about 1600° C. for a residence time of no greater than about 100 milliseconds to provide a product stream containing enhanced yields of acetylene. The product stream exits the outlet of pyrolysis zone 90 via line 110 and passes through cooling zone 120 and exits the cooling zone via line 140. The stream temperature is reduced from about 1500° C. (as measured at cooling zone inlet) to about 500° C. (as measured at cooling zone outlet) within about 100 milliseconds, say, within about 10 milliseconds. The cooled product stream is directed to a recovery zone (not shown) and is treated to recover reaction products. The cooled gaseous or vapor product stream contains about 9 wt % acetylene, about 27 wt % CO, about 11 wt % $CO_2$, about 2.5 wt % $H_2$, about 2 wt % $CH_4$, and about 20 wt % hydrocarbons heavier than acetylene.

While the present invention has been described and illustrated with respect to certain embodiments, it is to be understood that the invention is not limited to the particulars disclosed and extends to all equivalents within the scope of the claims.

What is claimed is:

1. A process for producing acetylene by pyrolysis from a feed stream of hydrocarbons comprised of coal particles having a median particle size of less than about 100 microns in diameter and a hydrocarbon co-feed material, said feed stream containing less than about 12 wt % atomic hydrogen, the process comprising:
   (a) blending the hydrocarbons containing less than about 12 wt % atomic hydrogen with methane to provide a blended mixture containing at least about 12.5 wt % atomic hydrogen;
   (b) partially combusting the blended mixture in a reactor in the presence of a source of oxygen, the oxygen being provided in an amount no greater than about 50 wt % of the stoichiometric amount required to fully combust all of the blended mixture to provide a partially combusted mixture at or above a temperature sufficient to produce methyl radicals;
   (c) maintaining the partially combusted mixture in the substantial absence of molecular oxygen at or above 2000° C. for a residence time of no greater than about 50 milliseconds to convert the mixture to a product stream containing enhanced yields of acetylene without significant formation of coke and/or coke precursors;
   (d) cooling the product stream to 500° C. or less within no greater than 100 milliseconds to substantially arrest any cracking reactions and provide a cooled product stream; and
   (e) recovering acetylene from the cooled product stream.

2. The process of claim 1 wherein at least a portion of acetylene derived from the cooled product stream is converted to ethylene by hydrogenation.

3. The process of claim 1 wherein the cooling is carried out by passing the product stream through at least one of a) a convergent-divergent nozzle, b) a gas turbine expander, c) an indirect heat exchanger, d) a direct liquid quench zone, and e) an endothermic reactant addition zone.

4. The process of claim 3 wherein the quench liquid in the direct liquid quench zone is selected from water and hydrocarbon.

5. The process of claim 3 wherein ethane is added to the endothermic reactant addition zone.

6. The process of claim 1 wherein the cooling is carried out by passing the product stream through a convergent-divergent nozzle in which the product stream is accelerated to a velocity of at least about 150 meters per second and decelerated to a velocity no greater than about 100 meters per second in the converging-diverging nozzle.

7. The process of claim 6 wherein the product stream is accelerated to a velocity ranging from about 150 to about 1220 meters per second and decelerated to a velocity ranging from about 45 to about 100 meters per second, the product stream being cooled in less than about 2 milliseconds, to provide a cooled product stream of no greater than about 260° C.

8. The process of claim 6 wherein a quench liquid is introduced between the convergent and divergent sections of the nozzle.

9. The process of claim 1 wherein the product stream is cooled in less than about 10 milliseconds to provide a cooled product stream of no greater than about 482° C.

10. The process of claim 9 wherein the product stream is accelerated to a velocity ranging from about 150 to about 1220 meters per second and decelerated to a velocity ranging from about 45 to about 100 meters per second, and the product stream is cooled in less than about 2 milliseconds, to provide a cooled product stream of no greater than about 260° C.

11. The process of claim 9 wherein the partially combusted mixture is maintained at or above 2000° C. for a residence time ranging from about 2 to about 30 milliseconds.

12. The process of claim 1 wherein step (c) is carried out in the presence of sufficient hydrogen to reduce formation of coke or coke precursors beyond that produced in the absence of hydrogen.

13. The process of claim 1 wherein the co feed material is selected from the group consisting of aromatic feed, gas oils, cracked gas oils, crude, atmospheric resid feed, vacuum resid feed, tars, heavy feed containing pitch, and mixtures thereof.

14. The process of claim 1 wherein the feed stream of hydrocarbons contains less than about 10 wt % atomic hydrogen.

15. The process of claim 1 wherein the feed stream of hydrocarbons contains less than about 8 wt % atomic hydrogen.

16. The process of claim 1 wherein syngas is also recovered from the cooled product stream.

17. The process of claim 1 wherein ethylene is also recovered from the cooled product stream.

18. The process of claim 1 wherein the partially combusted mixture is provided at or above a temperature sufficient to produce methyl radicals and hydrogen radicals.

* * * * *